United States Patent
Nishiguchi et al.

(10) Patent No.: US 6,469,059 B1
(45) Date of Patent: Oct. 22, 2002

(54) FUNGICIDAL COMPOSITION AND METHOD FOR DISEASE CONTROL OF PADDY-RICE PLANTS

(76) Inventors: Tsutomu Nishiguchi, 1395-1-203, Ichimachi, Kawachinagano-shi, Osaka-fu (JP); Sohkichi Tajima, 10-9-301, Nagai 2-chome, Sumiyoshi-ku, Osaka-shi, Osaka-fu (JP); Yoshinobu Yamamoto, 40-1-625, Mikanodai 1-chome, Kawachinagano-shi, Osaka-fu (JP)

( * ) Notice: Subject to any disclaimer, the term of this patent is extended or adjusted under 35 U.S.C. 154(b) by 0 days.

(21) Appl. No.: 09/339,791

(22) Filed: Jun. 24, 1999

(51) Int. Cl.⁷ .................. A01N 37/34; A01N 57/10; A01N 43/54; A01N 43/82; A01N 37/12
(52) U.S. Cl. ............... 514/521; 514/146; 514/275; 514/361; 514/373; 514/383; 514/391; 514/469; 514/538; 514/619; 514/634
(58) Field of Search ................. 514/538, 521, 514/391, 383, 275, 634, 619, 469, 373, 361, 146

(56) References Cited

FOREIGN PATENT DOCUMENTS

| CA | 1311240 | | 12/1992 |
|---|---|---|---|
| EP | 262393 | | 1/1993 |
| JP | 63132867 | * | 6/1988 |

OTHER PUBLICATIONS

Tom Lin, The Pesticide Manual Incorporating The Agrochemicals Handbook 10$^{th}$ Ed. (1995) p. 68.*

* cited by examiner

*Primary Examiner*—Allen J. Robinson

(57) ABSTRACT

A fungicidal composition for paddy-rice plants has as active ingredients N-(1-cyano-1,2-dimethylpropyl)-2-(2,4-dichlorophenoxy)propanamide in combination with one or more compounds selected from fungicidally active compounds. The combination is useful in a method for disease control of paddy-rice plants.

2 Claims, No Drawings

FUNGICIDAL COMPOSITION AND METHOD FOR DISEASE CONTROL OF PADDY-RICE PLANTS

BACKGROUND OF THE INVENTION

The present invention relates to a fungicidal composition for paddy-rice plants which exerts a synergistic effect, which cannot be derived from a sole or an extended fungicidal spectrum, to control damage by disease, by means of the blend of two or more different agents.

In order to control damage by disease of paddy-rice plants, fungicidal agents have been developed and used, such as, probenazole (common name) and tricyclazole (common name) against Blast (*Pyricularia oryzae*), dichlomezine (common name) and validamycin (common name) and the like against Sheath blight (*Rhizoctonia solani*), and ferimzone (common name), fthalide (commom name), iprodione (common name) and the like against Helminthosporium leaf spot (*Cochliobolus miyabeanus*).

Nowadays, aging of farm workers has further advanced and reduction of labor has been desired in any farming work. Also in the applying work of the agents for the purpose of controlling damage by disease of paddy-rice plants, in order to lighten the work, it has been earnestly desired to develop an agent having a broad fungicidal spectrum or a fungicidal composition which is useful in controlling various diseases without losing the characteristics of each active ingredient compound. However, the time to control each disease is not always the same, and the mere combined use cannot exert the desired effect to adequately control damage of disease.

SUMMARY OF THE INVENTION

In order to solve the above-mentioned problem, the present inventors have intensively studied to find an excellent effect to control damage by disease of paddy-rice plants by the synergistic action in addition to enlargement of the fungicidal spectrum by means of the use of N-(1-cyano-1,2-dimethylpropyl)-2-(2,4-dichlorophenoxy)propanamide (hereinafter referred to as compound A) in combination with fungicidally active compounds, and then, completed the present invention.

DESCRIPTION OF THE PREFERRED EMBODIMENTS

Compound A that is one hand of the active ingredient compounds in the present invention is described in Japanese Patent Application Laid-open No. Sho 63-132867, which also describes that it is useful as a fungicidal agent in agriculture and horticulture.

Compound A that is one hand of the active ingredient in the present invention has two chiral carbon atoms, and so it has four optional isomers. The present invention includes the individual optical isomer and the mixture of the aboubmentioned optical isomer.

For the fungicidally active compound that is the other hand of the active ingredient compounds, one or more compounds selected from the following ones may be used:
(1) α,α,α-trifluoro-3'-isopropoxy-O-toluanilide (common name: flutolanil; hereinafter referred to as compound 1);
(2) 3'-isopropoxy-2-methylbenzanilide (common name: mepronil hereinafter referred to as compound 2);
(3) N-(2,6-dibromo-4-trifluoromethoxyphenyl)-2-methyl-4-trifluoromethylthiazole-5-carboxamide (common name: thifluzamide; hereinafter referred to as compound 3);
(4) 5-chloro-1,3-dimethyl-N-(1,1-dimethyl-2-oxa-4-indanyl)pyrazole-4-carboxamide (common name: furametpyr; hereinafter referred to as compound 4);
(5) validamycin (common name; hereinafter referred to as compound 5);
(6) 1-(4-chlorobenzyl)-1-cyclopentyl-3-phenylurea (common name: pencycuron; hereinafter referred to as compound 6);
(7) 6-(3,5-dichloro-4-methylphenyl)-3(2H)-pyridazinone (common name: diclomezine; hereinafter referred to as compound 7);
(8) 3-(3,5-dichlorophenyl)-N-isopropyl-2,4-dioxoimidazolidine-1-carboxamide (common name: iprodione; hereinafter referred to as compound 8);
(9) 2-p-chlorophenyl-2-(1H-1,2,4-triazol-1-ylmethyl)hexanenitrile (common name: myclobutanil; hereinafter referred to as compound 9);
(10) (RS)-2-(2,4-dichlorophenyl)-1-(1H-1,2,4-triazol-1-yl)hexan-2-ol (common name: hexaconazole; hereinafter referred to as compound 10); (11) (Z)-2'-methylacetophenone 4,6-dimethylpyrimidin-2-ylhydrazone (common name: ferimzone; hereinafter referred to as compound 11);
(12) 1,1'-iminodi(octamethylene)diguanidinium triacetate (common name: guazatine; hereinafter referred to as compound 12);
(13) methyl (E)-2- {2-[6-(2-cyanophenoxy)pyrimidin-4-yloxy]phenyl}-3-methoxy-acrylate (common name: azoxystrobin; hereinafter referred to as compound 13);
(14) 2-methoxyimino-N-methyl-2-(2-phenoxy)phenylacetamide (code name: SSF-126; hereinafter referred to as compound 14);
(15) diisopropyl-1,3-dithiolan-2-ylidenemalonate (common name: isoprothiolane; hereinafter referred to as compound 15);
(16) O-ethyl-S,S-diphenyldithiophosphate (common name: Hinosan; hereinafter referred to as compound 16);
(17) 5-methyl-1,2,4-triazolo[3,4-b]benzothiazole (common name: tricyclazole; hereinafter referred to as compound 17);
(18) 4,5,6,7-tetra-chlorophthalide (common name: fthalide; hereinafter referred to as compound 18);
(19) kasugamycin (hereinafter referred to as compound 19);
(20) N-[1-(4-chlorophenyl)ethyl]-2,2-dichloro-1-ethyl-3-methyl-cyclopropanecarboxamide (common name carpropamid; hereinafter referred to as compound 20);
(21) N-[1-(2,4-dichlorophenyl)ethyl]-2-cyano-3,3-dimethylbuthaneamide (hereinafter referred to as compound 21);
(22) 1,2,5,6-tetrahydropyrrolo(3,2,1-i,j)quinolin-4-one (common name: pyroquilon; hereinafter referred to as compound 22);
(23) 3-allyloxy-1,2-benzoisothiazole-1,1-dioxide (common name: probenazole; hereinafter referred to as compound 23); and
(24) S-methyl-benzo(1,2,3)-thiadiazole-7-carbothiolate (code name: CGA-245704; hereinafter referred to as compound 24).

The fungicidal composition for paddy-rice plants of the present invention may incorporate from 0.01 to 80 parts by weight of the sum of compound A and the fungicidally active compounds in 100 parts by weight of the composition, preferably from 1 to 70 and the incorporating ratio of the fungicidally active compounds is normally from 0.01 to 1000 parts by weight to 1 part by weight of compound A (1:0.01 to 1:1000), preferably from 1:100 to 50:1 parts by weight, more preferably from 1:50 to 20:1 parts by weight.

When the composition of the present invention is used as a fungicidal agent for paddy-rice plants, normally, the active substances may be mixed with solid or liquid carriers, and if needed, surface active agents or other adjuvants for the preparations may be added to prepare oil solution, emulsifiable concentrates, wettable powders, granules, dusts, liquid formation, suspensions, foams, microcapsules, ULV, pastes and the like for use. These preparations contain from 0.1 to 99.9 wt. %, preferably from 0.2 to 80 wt. % of the active ingredients in total. These preparations may be obtained by, for instance, mixing the active ingredients with spreaders, that is, solid carriers, or liquid carriers, or, if necessary, surface active agents, sticking agents, dispersing agents, stabilizers, foaming agent and the like, or the mixture thereof.

The solid carriers may be exemplified by fine powders or granules of clays (kaolin, diatomaceous earths, synthetic hydrous silicon oxide, clay, bentonite, acid clay, etc.), talcs, and other inorganic minerals ( sericite, quartz powders, sulfur powders, active carbon, calcium carbonate, hydrous silica, etc. ). The liquid carriers may be exemplified by water, alcohols (methanol, ethanol, etc.), ketones (acetone, methyl ethyl ketone, etc.), aromatic hydrocarbons (benzene, toluene, xylene, ethylbenzene, methylnaphthalene, etc.), aliphatic hydrocarbons (n-hexane, cyclohexane, kerosine, kerosene, etc.), esters (ethyl acetate, butyl acetate, etc.), nitriles (acetonitrile, isobutyronitrile, etc.), ethers (dioxane, diisopropyl ether, etc.), acid amides (dimethylformamide, dimethylacetamide, etc.), and halogenated hydrocarbon (dichloroethane, trichloroethylene, etc.).

The surface active agents may be exemplified by alkyl sulfates, alkyl sulfonates, alkylaryl sulfonates, alkyl aryl ethers and polyoxyethylenated substances thereof, polyethylene glycol ethers, polyhydric alcohol esters, sugar alcohol derivatives and the like. The other adjuvants for the preparations may be exemplified by sticking agents and dispersing agents such as casein, gelatin, polysaccharide (starch, gum arabic, cellulose derivatives, alginic acid etc.), lignin derivatives, bentonite, synthetic water-soluble polymer (polyvinyl alcohol), polyvinylpyrrolidone, poly(acrylic acid), etc.) and the like, and stabilizers such as PAP (acidic isopropyl phosphate), BHT (2,6-di-t-butyl-4-methylphenol), vegetable oils, mineral oils, fatty acids, fatty acid esters and the like.

When the fungicidal composition for paddy-rice plants of the present invention is used to control damage of disease of paddy-rice plants, it may be used as such or following dilution with water and the like for foliar treatment, water treatment, soil treatment or treatment of seedling culture boxes. And it may be used in combination with other fungicides, insecticides, herbicides, fertilizers, or soil improving agents.

Compound A that is one hand of the active ingredient compounds in the present invention exerts the same effect as that in the present invention even when used in combination with insecticides, and the insecticides may be exemplified by 1,3-bis(carbamoylthio)-2-(N,N-dimethylamino)propane hydrochloride (common name: cartap),
1-(6-chloro-3-pyridylmethyl)-N-nitroimidazolidin-2-ylidenamine (common name: imidacloprid),
4,5-dihydro-6-methyl-4-(3-pyridylmethyleneamino)-1,2,4-triazin-3(2H)-one (common name: pymetrozine),
ethyl N-[2,3-dihydro-2,2-dimethylbenzofuran-7-yloxycarbonyl(methyl)aminothio]-N-isopropyl-β-alaninate (common name: benfuracarb),
2,3-dihydro-2,2-dimethyl-7-benzofuranyl[(dibutylamino)thio]-methylcarbamate (common name: carbosulfan),
(E)-N-(6-chloro-3-pyridylmethyl)-N-ethyl-N'-methyl-2-nitrovinylidendiamine (common name: nitenpyram),
p-methylthiophenyl dipropyl phosphate (common name: propaphos),
N-t-butyl-N'-(4-ethylbenzoyl)-3,5-dimethylbenzohydrazide (common name: tebufenozide),
2-t-butylimino-3-isopropyl-5-phenyl-3,4,5,6-tetrahydro-2H-1,3,5-thiadiazin-4-one (common name: buprofezine).
2-(4-ethoxyphenyl)-2-methylpropyl 3-phenoxybenzyl ether (common name: ethofenprox),
0,0-dimethyl-O-3,5,6-trichloro-2-pyridylphosphorothioate (common name: chlorpyrifos-methyl),
dimethyl 4-nitro-m-tolyl phosphorothioate (common name: MEP),
4-ethoxyphenyl-[3-(4-fluoro-3-phenoxyphenyl)propyl]-dimethylsilane (common name: silafluofen),
2-secondary-butylphenyl-N-methylcarbamate (common name: BPMC),
S-(α-(ethoxycarbonyl)benzyl)dimethyl phosphorodithioate (common name: PAP),
0,0-diethyl-0-(5-phenyl-3-isooxazolyl)phosphorothioate (common name: isoxathion),
dimethyl 4-methylthio-m-tolyl phosphorothiate (common name: MPP),
(RS)-α-cyano-3-phenoxybenzyl(RS)-2,2-dichloro-1-(4-ethoxyphenyl)cyclopropanecarboxylate (common name: cycloprothrin) and the like.

The quantity of the composition of the present invention to be used depends upon the compounding ratio of the active ingredients, the weather conditions, the form of the preparations, the time to be used, the way to use, the place to be used, the disease to be controlled and the like, and in general, from 0.1 to 1000 g, preferable from 1 to 50 g of the active ingredients per an are is used. When the emulsifiable concentrates, wettable powders, suspensions, liquid formation, and the like is applied by being diluted with a predetermined amount of water, the concentration of the active ingredients in the diluted solution is from 0.0001 to 0.1%. The granules, dusts and the like is normally applied without being diluted with water.

The disease of paddy-rice plants that the composition of the present invention exerts the effect to control is exemplified by Blast (*Pyricularia oryzae*), Sheath blight (*Rhizoctonia solani*), Helminthosporium leaf spot (*Cochliobolus miyabeanus*), Cercospora leaf spot (*Spharulina oryzina*), Stem-rot (*Leptosphaeria slavini*), colored rice and the like.

EXAMPLE

The following are the typical examples of the formulation examples and test examples. In the following examples, part(s) means part(s) by weight.

Formulation Example 1

Wettable Powders

| | |
|---|---|
| Compound A | 1 part |
| One of the compounds 1 to 24 | 10 parts |

-continued

| | |
|---|---|
| Calcined diatomaceous earth | 72 parts |
| Polyoxyethylene nonylphenyl ether | 5 parts |
| Condensation products of naphthalenesulfonic acid and formalin | 4 parts |
| Hydrous silicic acid | 8 parts |

The above ingredients are homogeneously mixed together and ground to form wettable powders.

Formulation Example 2

Wettable Powders

| | |
|---|---|
| Compound A | 1 part |
| One of the compounds 1 to 24 | 50 parts |
| Calcined diatomaceous earth | 32 parts |
| Polyoxyethylene nonylphenyl ether | 5 parts |
| Condensation products of naphthalenesulfonic acid and formalin | 4 parts |
| Hydrous silicic acid | 8 parts |

The above ingredients are homogeneously mixed together and ground to form wettable powders.

Formulation Example 3

Wettable Powders

| | |
|---|---|
| Compound A | 5 parts |
| One of the compounds 1 to 24 | 10 parts |
| Calcined diatomaceous earth | 68 parts |
| Polyoxyethylene nonylphenyl ether | 5 parts |
| Condensation products of naphthalenesulfonic acid and formalin | 4 parts |
| Hydrous silicic acid | 8 parts |

The above ingredients are homogeneously mixed together and ground to form wettable powders.

Formulation Example 4

Wettable Powders

| | |
|---|---|
| Compound A | 20 parts |
| One of the compounds 1 to 24 | 1 part |
| Calcined diatomaceous earth | 62 parts |
| Polyoxyethylene nonylphenyl ether | 5 parts |
| Condensation products of naphthalenesulfonic acid and formalin | 4 parts |
| Hydrous silicic acid | 8 parts |

The above ingredients are homogeneously mixed together and ground to form wettable powders.

Formulation Example 5

Wettable Powders

| | |
|---|---|
| Compound A | 20 parts |
| One of the compounds 1 to 24 | 5 parts |
| Calcined diatomaceous earth | 58 parts |
| Polyoxyethylene nonylphenyl ether | 5 parts |
| Condensation products of naphthalenesulfonic acid and formalin | 4 parts |
| Hydrous silicic acid | 8 parts |

The above ingredients are homogeneously mixed together and ground to form wettable powders.

Formulation Example 6

Wettable Powders

| | |
|---|---|
| Compound A | 10 parts |
| One of the compounds 1 to 24 | 1 part |
| Calcined diatomaceous earth | 72 parts |
| Polyoxyethylene nonylphenyl ether | 5 parts |
| Condensation products of naphthalenesulfonic acid and formalin | 4 parts |
| Hydrous silicic acid | 8 parts |

The above ingredients are homogeneously mixed together and ground to form wettable powders.

Formulation Example 7

Granules

| | |
|---|---|
| Compound A | 1 part |
| One of the compounds 1 to 24 | 20 parts |
| Hydrous silicic acid | 1 part |
| Calcium lignin sulfonate | 2 parts |
| Bentonite | 30 parts |
| Kaolin clay | 4 parts |

The above ingredients are homogeneously mixed together and ground, incorporated with a proper quantity of water and, kneaded. The resulting mixture was granulated and dried to form granules.

Formulation Example 8

Granules

| | |
|---|---|
| Compound A | 5 parts |
| One of the compounds 1 to 24 | 5 parts |
| Hydrous silicic acid | 3 parts |
| Calcium lignin sulfonate | 2 parts |
| Bentonite | 30 parts |
| Kaolin clay | 55 parts |

The above ingredients are homogeneously mixed together and ground, incorporated with a proper quantity of water and,kneaded. The resulting mixture was granulated and dried to form granules.

Formulation Example 9

Granules

| | |
|---|---|
| Compound A | 1 part |
| One of the compounds 1 to 24 | 5 parts |
| Hydrous silicic acid | 3 parts |
| Calcium lignin sulfonate | 2 parts |
| Bentonite | 30 parts |
| Kaolin clay | 59 parts |

The above ingredients are homogeneously mixed together and ground, incorporated with a proper quantity of water and, kneaded. The resulting mixture was granulated and dried to form granules.

Formulation Example 10

Granules

| | |
|---|---|
| Compound A | 4 parts |
| One of the compounds 1 to 24 | 1 part |
| Hydrous silicic acid | 1 part |
| Calcium lignin sulfonate | 2 parts |
| Bentonite | 30 parts |
| Kaolin clay | 62 parts |

The above ingredients were homogeneously mixed and ground, kneaded with a proper quantity of water, granulated, and dried to form granules.

Test Example 1

Preventive Effect by Application Against Blast (*Pyricularia oryzae*)

The wettable powder prepared according to the Formulation Examples were diluted with water to a predetermined concentration and sprayed over the stems and leaves of a six-leave-stage rice plant (Kin-maze) cultivated in pots under flooding. After air-drying, the spore suspension of Blast (*Pyricularia oryzae*) was sprayed and inoculated on the plant. After that, the plant was allowed to stand under humid conditions at 20° C. for on week, and then, the number of the disease lesion was predetermined to obtain the preventive index according to the following criterion. The result is shown in Table 1.

[Criterion]

| Preventive index | Preventive effect |
|---|---|
| 5 | Preventive value 95% or more |
| 4 | Preventive value 85 to 94% |
| 3 | Preventive value 60 to 84% |
| 9 | Preventive value 40 to 59% |
| 1 | Preventive value 1 to 39% |

TABLE 1

| Test compound | Concentration of active ingredients (ppm) | Preventive index |
|---|---|---|
| Compound A + Compound 1 | 10 + 500 | 5 |
| Compound A + Compound 2 | 10 + 500 | 5 |
| Compound A + Compound 3 | 10 + 500 | 5 |
| Compound A + Compound 5 | 10 + 500 | 5 |
| Compound A + Compound 6 | 10 + 500 | 5 |
| Compound A + Compound 11 | 5 + 50 | 5 |
| Compound A + Compound 13 | 5 + 10 | 5 |
| Compound A + Compound 14 | 5 + 50 | 5 |
| Compound A + Compound 15 | 5 + 50 | 5 |
| Compound A + Compound 16 | 5 + 50 | 5 |
| Compound A + Compound 17 | 5 + 5 | 5 |
| Compound A + Compound 18 | 5 + 5 | 5 |
| Compound A + Compound 20 | 5 + 5 | 5 |
| Compound A + Compound 21 | 5 + 5 | 5 |
| Compound A | 10 | 4 |
| Compound A | 5 | 4 |
| Compound 1 | 500 | 0 |
| Compound 2 | 500 | 0 |
| Compound 3 | 500 | 0 |
| Compound 5 | 500 | 0 |
| Compound 6 | 500 | 0 |
| Compound 11 | 50 | 3 |
| Compound 13 | 10 | 4 |
| Compound 14 | 50 | 4 |
| Compound 15 | 50 | 4 |
| Compound 16 | 50 | 3 |
| Compound 17 | 5 | 4 |
| Compound 18 | 5 | 3 |
| Compound 20 | 5 | 4 |
| Compound 21 | 5 | 4 |

Test Example 2

Preventive Effect by Paddy Water Application Against Blast (*Pyricularia oryzae*)

By using pots of 1/14000 are, the granules prepared according to the Formulations Examples were water-applied to six-leave-stage rice plant (Kin-maze) cultivated under flooding. The treated pots were allowed to stand in a greenhouse for seven days, and the spore suspension of Blast (*Pyricularia oryzae*) was sprayed and inoculated on the plant. Then, the plant was allowed to stand under humid conditions at 20° C. for one week, and then, the number of the diseaselesion was determined to obtain the preventive index according to the criterion of Test Example 1. The result is shown in Table 2.

TABLE 2

| Test compound | Concentration of active ingredients (g/10a) | Preventive index |
|---|---|---|
| Compound A + Compound 1 | 10 + 200 | 4 |
| Compound A + Compound 4 | 10 + 200 | 4 |
| Compound A + Compound 13 | 10 + 10 | 4 |
| Compound A + Compound 14 | 10 + 50 | 4 |
| Compound A + Compound 22 | 10 + 10 | 5 |
| Compound A + Compound 23 | 10 + 50 | 5 |
| Compound A + Compound 24 | 10 + 50 | 5 |
| Compound A | 10 | 3 |
| Compound 1 | 200 | 0 |
| Compound 4 | 200 | 0 |
| Compound 13 | 10 | 3 |
| Compound 14 | 50 | 3 |

TABLE 2-continued

| Test compound | Concentration of active ingredients (g/10a) | Preventive index |
|---|---|---|
| Compound 22 | 10 | 4 |
| Compound 23 | 50 | 3 |
| Compound 24 | 50 | 3 |

Test Example 3

Treatment Effect by Application Against Blast (*Pyricularia oryzae*)

To six-leave-stage rice plant (Kin-maze) cultivated in pots under flooding, the spore suspension of Blast (*Pyricularia oryzae*) was sprayed and inoculated. After the inoculation, the wettable powders according to the Formulation Examples which were diluted with water to a predetermined concentration were sprayed over the stems and leaves of the plant under humid conditions at 20° C. for one day. After air-drying, the plant was allowed to stand under humid conditions for one week, and then, the number of the disease lesion was determined to obtain the preventive index according to the criterion of Test Example 1. The result is shown in Table 3.

TABLE 3

| Test compound | Concentration of active ingredients (ppm) | Preventive index |
|---|---|---|
| Compound 1 + Compound 19 | 200 + 20 | 5 |
| Compound 1 | 200 | 0 |
| Compound 19 | 20 | 4 |

Test Example 4

Preventive Effect by Application Against Sheat Blight (*Rhizoctonia solani*)

The wettable powders prepared according to the Formulation Examples which were diluted with water to a predetermined concentrations were sprayed to the stems and leaves of ten-leave-stage of rice plant (Kin-maze) cultivated in pots under flooding. After air-drying, the fungous nucleiof Sheath blight (*Rhizoctonia solani*) was inoculated at the root of the plant. After that, the plant was allowed to stand under humid conditions at 30° C. for one week, and then, the number of the disease lesion was determined to obtain the preventive index according to the criterion of Test Example 1. The result is shown in Table 4.

TABLE 4

| Test compound | Concentration of active ingredients (ppm) | Preventive index |
|---|---|---|
| Compound A + Compound 1 | 200 + 10 | 4 |
| Compound A + Compound 2 | 200 + 10 | 3 |
| Compound A + Compound 3 | 200 + 10 | 4 |
| Compound A + Compound 5 | 200 + 10 | 4 |
| Compound A + Compound 6 | 200 + 10 | 4 |

TABLE 4-continued

| Test compound | Concentration of active ingredients (ppm) | Preventive index |
|---|---|---|
| Compound A + Compound 7 | 200 + 10 | 3 |
| Compound A + Compound 13 | 200 + 10 | 4 |
| Compound A + Compound 14 | 200 + 50 | 4 |
| Compound A | 200 | 0 |
| Compound 1 | 10 | 3 |
| Compound 2 | 10 | 2 |
| Compound 3 | 10 | 3 |
| Compound 5 | 10 | 3 |
| Compound 6 | 10 | 3 |
| Compound 7 | 10 | 2 |
| Compound 13 | 10 | 3 |
| Compound 14 | 50 | 3 |

Test Example 5

Preventive Effect by Paddy Water Application Against Sheath Blight (*Rhizoctonia solani*)

By using pots of 1/5000 are, the compounds prepared according to the Formulations Examples which were diluted with water to a predetermined concentration were water-applied to ten-leave-stage rice plant (Kin-maze) cultivated under flooding. The treated pots were allowed to stand in a greenhouse for seven days, and the fungus nuclei of Sheath blight (*Rhizoctonia solani*) was inoculated at the root of the plant. Then, the plant was allowed to stand under humid conditions at 30° C. for one week, and then, the number of the disease lesion was determined to obtain the preventive index according to the criterion of Test Example 1. The result is shown in Table 5.

TABLE 5

| Test compound | Concentration of active ingredients (g/10a) | Preventive index |
|---|---|---|
| Compound A + Compound 8 | 200 + 10 | 4 |
| Compound A + Compound 9 | 200 + 10 | 3 |
| Compound A + Compound 10 | 200 + 10 | 4 |
| Compound A + Compound 11 | 200 + 10 | 4 |
| Compound A + Compound 12 | 200 + 10 | 4 |
| Compound A | 200 | 0 |
| Compound 8 | 10 | 3 |
| Compound 9 | 10 | 3 |
| Compound 10 | 10 | 3 |
| Compound 11 | 10 | 3 |
| Compound 12 | 10 | 3 |

Test Example 6

Preventive Effect by Application Against Helminthosporium Leaf Spot (*Cochliobolus miyabeanus*)

The wettable powder prepared according to the Formulation Examples which were diluted with water to a predetermined concentration were sprayed over the stems and leaves of six-leave-stage rice plant (Kin-maze) cultivated in pots under flooding. After air-drying, the spore suspension of Helminthosprium leaf spot (*Cochliobolus miyabeanus*)

was sprayed and inoculated on the plant. After the inoculation, the plant was allowed to stand under humid conditions at 20° C. for one week, and then, the number of the disease lesion was determined to obtain the preventive index according to the criterion of Test Example 1. The result is shown in Table 6.

TABLE 6

| Test compound | Concentration of active ingredients (ppm) | Preventive index |
| --- | --- | --- |
| Compound A + Compound 8 | 200 + 10 | 4 |
| Compound A + Compound 9 | 200 + 10 | 4 |
| Compound A + Compound 10 | 200 + 10 | 4 |
| Compound A + Compound 11 | 200 + 10 | 4 |
| Compound A + Compound 12 | 200 + 10 | 4 |
| Compound A + Compound 13 | 200 + 10 | 4 |
| Compound A + Compound 14 | 200 + 50 | 4 |
| Compound A | 200 | 0 |
| Compound 8 | 10 | 3 |
| Compound 9 | 10 | 3 |
| Compound 10 | 10 | 3 |
| Compound 11 | 10 | 3 |
| Compound 12 | 10 | 3 |
| Compound 13 | 10 | 3 |
| Compound 14 | 50 | 3 |

What is claimed is:

1. A fungicidal composition for paddy-rice plants comprising a synergistic fungicidally effect amount of N-(1-cyano-1,2-dimethylpropyl)-2-(2,4-dichlorophenoxy) propanamide, and one or more compounds selected from the group consisting of iprodione, hexaconazole, ferimzone, guazatine, azoxystrobin; metominostrobin, edifenpbos, fthalide, probenazole and acibenzoloar-S-methyl, wherein the content of the one or more compounds is from 0.01 to 1000 parts by weight to 1 part by weight of N-(1-cyano-1, 2-dimethylpropyl)-2-(2,4-dichlorophenoxy)propanamide.

2. A method of disease control of paddy-rice plants, the method comprising: treating a rice paddy with an effective amount of a fungicidal composition for paddy-rice plants which contains a synergistic fungicidally effective amount of N-(1-cyano-1,2-dimethylpropyl)-2-(2,4-dichlorophenoxy)propanamide, and one or more compounds selected from the group consisting of iprodione, hexaconazole, ferimzone, guazatine, azoxystrobin, metominostrobin, edifenphos, fthalide, probenazole and acibenzoloar-S-methyl, wherein the content of the one or more compounds is from 0.01 to 1000 parts by weight to 1 part by weight of N-(1-cyano-1,2-dimethylpropyl)-2-(2,4-dichlorophenoxy)propanamide.

* * * * *

UNITED STATES PATENT AND TRADEMARK OFFICE
CERTIFICATE OF CORRECTION

PATENT NO.    : 6,469,059 B1
DATED         : October 22, 2002
INVENTOR(S)   : Nishiguchi et al.

It is certified that error appears in the above-identified patent and that said Letters Patent is hereby corrected as shown below:

<u>Title page,</u>
Insert the following:
-- [73] Assignee:  BASF Aktiengesellschaft Ludwigshafen (DE) --.
-- [74] *Attorney, Agent, or Firm* - Keil & Weinkauf --.

Signed and Sealed this

Eighteenth Day of February, 2003

JAMES E. ROGAN
*Director of the United States Patent and Trademark Office*